(12) United States Patent
Kychakoff et al.

(10) Patent No.: US 6,909,816 B2
(45) Date of Patent: Jun. 21, 2005

(54) SENSING SYSTEM FOR DETECTION AND CONTROL OF DEPOSITION ON PENDANT TUBES IN RECOVERY AND POWER BOILERS

(75) Inventors: George Kychakoff, Maple Valley, WA (US); Martin A Afromowitz, Mercer Island, WA (US); Richard E Hugle, Olympus, WA (US)

(73) Assignee: Combustion Specialists, Inc., Maple Valley, WA (US)

( * ) Notice: Subject to any disclaimer, the term of this patent is extended or adjusted under 35 U.S.C. 154(b) by 503 days.

(21) Appl. No.: 10/168,277

(22) PCT Filed: Dec. 14, 2000

(86) PCT No.: PCT/US00/33879

§ 371 (c)(1),
(2), (4) Date: Jun. 14, 2002

(87) PCT Pub. No.: WO01/44747

PCT Pub. Date: Jun. 21, 2001

(65) Prior Publication Data

US 2003/0021461 A1 Jan. 30, 2003

Related U.S. Application Data

(60) Provisional application No. 60/170,839, filed on Dec. 14, 1999.

(51) Int. Cl.[7] .................................................. G06K 9/36
(52) U.S. Cl. ........................ 382/285; 382/173; 382/141
(58) Field of Search .................................. 382/100, 141, 382/173, 224, 154, 264, 285; 431/12, 13, 75; 110/186, 234; 162/30.1, 30.11; 250/316.1, 330, 333

(56) References Cited

U.S. PATENT DOCUMENTS

| | | | | |
|---|---|---|---|---|
| 4,539,588 A | * | 9/1985 | Ariessohn et al. | 348/164 |
| 5,010,827 A | * | 4/1991 | Kychakoff et al. | 110/185 |
| 5,139,412 A | * | 8/1992 | Kychakoff et al. | 431/12 |
| 5,219,226 A | * | 6/1993 | James | 374/124 |
| 5,355,845 A | * | 10/1994 | Burgess et al. | 122/504 |
| 5,368,471 A | * | 11/1994 | Kychakoff et al. | 431/12 |
| 5,462,358 A | * | 10/1995 | Werner | 374/124 |
| 5,578,995 A | * | 11/1996 | Bryant et al. | 340/627 |

\* cited by examiner

*Primary Examiner*—Yon J. Couso
(74) *Attorney, Agent, or Firm*—J. Michael Neary (57) ABSTRACT

A system for detection and control of deposition on pendant tubes in recovery and power boilers includes one or more deposit monitoring sensors operating in infrared regions and about 4 or 8.7 microns and directly producing images of the interior of the boiler. An image pre-processing circuit (95) in which a 2-D image formed by the video data input is captured, and includes a low pass filter for performing noise filtering of said video input. An image segmentation module (105) for separating the image of the recovery boiler interior into background, pendant tubes, and deposition. An image-understanding unit (115) matches derived regions to a 3-D model of said boiler. It derives a 3-D structure the deposition on pendant tubes in the boiler and provides the information about deposits to the plant distributed control system (130) for more efficient operation of the plant pendant tube cleaning and operating systems.

6 Claims, 8 Drawing Sheets

SENSING SYSTEM FOR DETECTION AND CONTROL OF DEPOSITION ON PENDANT TUBES IN RECOVERY AND POWER BOILERS

This is related to U.S. Provisional Application No. 60/170,839 filed on Dec. 14,1999 and to PCT/US00/33879 filed on Dec. 14, 2000, and entitled "Sensing system for Detection and Control of Deposition on Pendant Tubes in Recovery and Power Boilers."

The U.S. Government has a paid-up license in this invention and the right in limited circumstances to require the patent owner to license others on reasonable terms as provided for by the terms of Contract No. DE-FC36-99G010375 by the Department of Energy.

This invention pertains to a sensing system for detection and control of deposition on pendant tubes in Kraft recovery boilers, and more particularly to a mid-band infra-red imaging system that is tuned to a particular spectrum of infra-red radiation to see into the otherwise visually impenetrable interior of a recovery boiler in operation to provide information about the condition of pendant steam tubes in the boiler.

BACKGROUND OF THE INVENTION

In 1995, about 82% of the wood pulp consumed at US paper and paperboard plants was produced using the Kraft process. Although the proportion of pulp from this source is likely to decline as new processes come on line, it is expected that well over 50% of wood pulp production will still be produced in 2020 using the Kraft process.

In the Kraft pulp production process, a fibrous material, most commonly wood chips, are broken down into pulp in a digester under pressure in a steam-heated aqueous solution of sodium hydroxide and sodium sulfide, called white liquor. After cooking in the digester, the pulp is separated from the residual liquid called black liquor. Black liquor is an aqueous solution containing wood lignins, organic material, and inorganic compounds oxidized in the digester during the cooking process. It is concentrated and then burned in a recovery boiler to generate steam, which is used in the pulp mill for pulp cooking and drying, and other energy requirements. The material remaining after combustion of the black liquor, called smelt, is collected in a molten bed at the bottom of the boiler and discharged to a dissolving tank to be recycled into new white liquor.

Kraft chemical and energy recovery boilers, in which the black liquor is burned, are large and expensive, with capacities installed in the last 30 years for pulp mills typically exceeding 1000 tons of pulp per day. It is difficult economically to add small incremental units of boiler capacity, so the capacity of the chemical recovery boiler is often the factor limiting the capacity of the entire pulp mill.

The effective burning capacity of recover boilers is frequently determined by the processes governing the deposition of fume, intermediate sized particles, and carryover of partially burnt liquor/smelt drops on heat transfer surfaces of the steam and water tubes in the boiler, and the attendant plugging of gas passages between and around those pendant steam and water tubes. Much effort has been made and continues to be made to improving the understanding of the mechanism of particulate and vapor deposition on the tubes. However, there are still no reliable on-line methods for systematically detecting the presence and build-up rates of these deposits.

Various efforts to control the rate and quantity of deposits on the pendant tubes in the boiler have been undertaken in the past. These include adjustments to conditions of combustion, such as the nozzles that spray the black liquor into the combustion chamber, and the way air is introduced into the combustion chamber. They also include systems, such as soot blowers, for removing deposits on the tubes before they seriously impact the operation of the boiler. These control efforts are most effective when they are immediately correlated to the results they produce, but heretofore there has been no reliable method of determining directly the amount of deposits on the pendant tubes. Such control efforts have therefore necessarily been based on indirect measurements and considerations, and have usually yielded unsatisfactory results.

The severe environment of boilers, namely the high temperature, turbulent gas flow, particle laden atmosphere, and intensity of radiation have made it difficult to develop a sensing system for detection and control of deposition on pendant tubes in Kraft recovery boilers that would be economically viable as a commercial product. Attempts to use near-IR cameras for direct monitoring of pendant tube deposits have failed to reliably produce good images over the span of large boilers, and devices operating at longer wavelengths have been impractical for boiler-side use because of prohibitive expense and the need for reliable cryogenic cooling.

U.S. Pat. No. 4,539,588 entitled "Imaging of Hot Infrared Emitting Surfaces Obscured by Particulate Fume and Hot Gasses" issued on Sep. 3, 1985 to Peter C. Ariessohn and R. K. James discloses an improvement in the technology of the time, but operated in a wavelength region of 1.5–1.8 micron, which has a relatively high susceptibility to light scattering by particles in the boiler gas stream.

Thus, there has long been a serious need for a deposition detection system for recovery boiler pendant tubes to solve the unfulfilled requirement to monitor the degree and distribution of fume, intermediate sized particles, and carryover particle depositions on recovery boiler tubes.

SUMMARY OF THE INVENTION

Accordingly, this invention provides a method of directly monitoring the depositions on recovery boiler pendant tubes.

The invention includes a focal plane array camera capable of creating images in a particular range of infrared radiation that has low absorption by molecules in the gas stream in a chemical recovery boiler, and is not scattered significantly by particles normally present in the boiler gas stream. Another aspect of the invention is a system of one or more deposit monitoring sensors feeding signals to a data processing system under control of a distributed control system. Preferably, the deposit monitoring sensors include focal plane array cameras operating in the mid-infra-red band, in the region of about 4–12 microns wavelength. Clear images can be obtained at a low cost of the boiler interior and particularly of the pendant water and steam tubes in the boiler to enable for the first time a visual real time inspection of the condition of the tubes and depositions thereon so that control schemes can be implemented.

DESCRIPTION OF THE DRAWINGS

The invention and its many attendant features and advantages will become clear upon reading the following detailed description of the preferred embodiment, in conjunction with the following drawings, wherein.

DESCRIPTION OF THE PREFERRED EMBODIMENT

Figure 1:
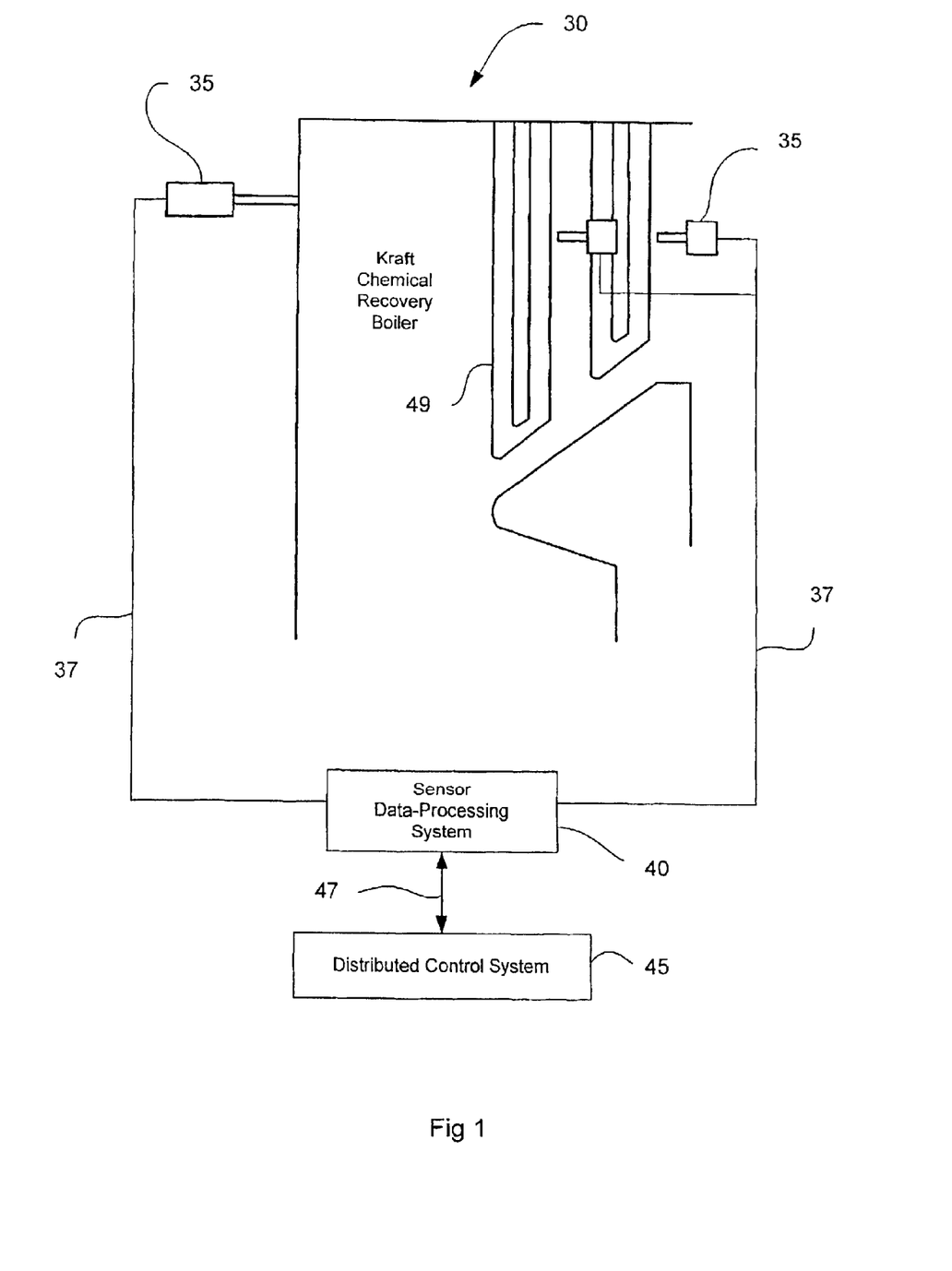
FIG. 1 is a schematic diagram of the invention installed in a Kraft recovery boiler.

Turning now to the drawings, and more particularly to FIG. 1 thereof, a deposition detection system in accordance with this invention is shown installed in a Kraft recovery boiler 30. The deposition detection system includes one or several monitoring sensors 35, described in detail below, which acquire data in the midband infra-red spectrum within a particular field of view from the interior of the recovery boiler. The monitoring sensors 35 could be fixed in position to permanently monitor particular areas within the boiler, or could be integrated hand-held units 36 shown in FIG. 3.

The sensor 35, shown in more detail in FIGS. 2 and 5–7, converts the acquired infrared data to electrical signals, which are conducted via electrical lines 37 to a sensor data processing system 40, shown in more detail in FIG. 10 and described in detail below. The hand-held sensor 36 shown in FIG. 3 converts the acquired infrared data directly to an image that is viewed on a display inside a hood 42 at the viewer end of a camera body 44.

A distributed control system 45, which is the computer system used by paper mill or power plant operators for controlling the operation of the plant, is connected to the sensor data processing system 40 by a link 47 for advanced control of the boiler operations in accordance with the information supplied by the sensor data processing system 40, with operator judgement and analysis where necessary, to minimize deposition of the pendant steam tubes 49 and otherwise maximize plant efficiency.

Figure 2:
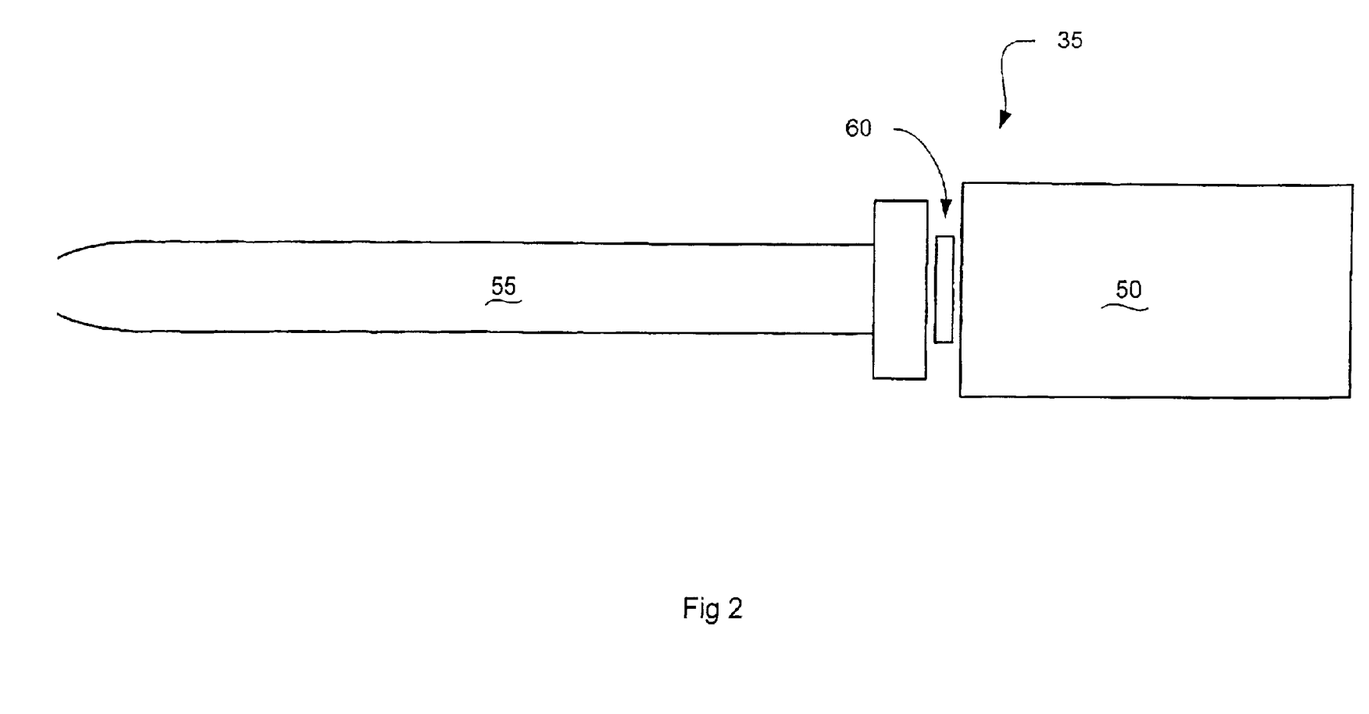
FIG. 2 is a schematic elevation of a monitoring sensor shown in FIG. 1.

Turning now to FIG. 2, one embodiment of the deposit monitoring sensor 35 is shown having a focal plane array camera 50 and a lens tube 55 connected to the camera 50 by way of a spectral band-pass filter 60 that limits the light admitted into the camera 50 to a particular band in the mid-IR spectrum.

Figure 5:
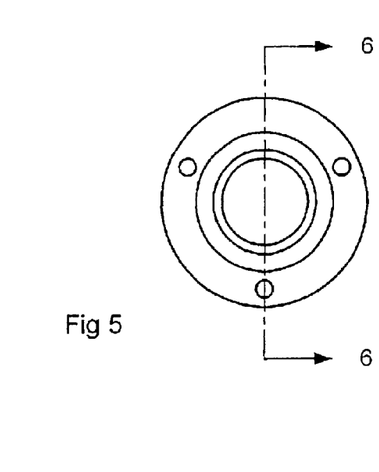
FIG. 5 is a sectional end elevation of the a monitoring sensors shown in FIG. 2.
Figure 6:
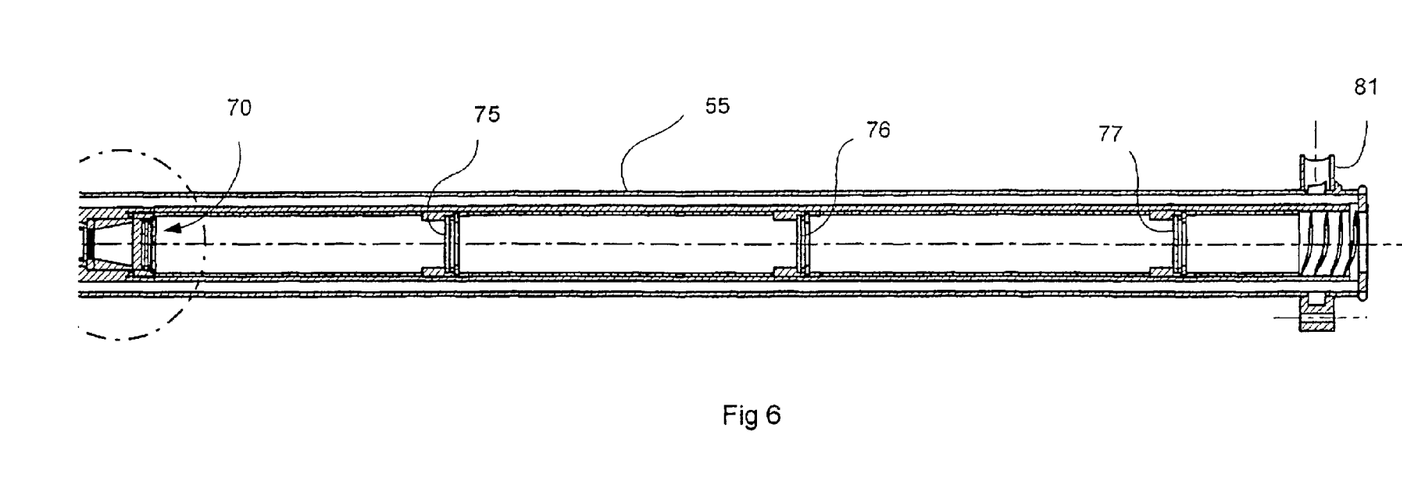
FIG. 6 is a sectional elevation of the a monitoring sensor shown in FIG. 3 along lines 6—6 in FIG. 4.
Figure 7:
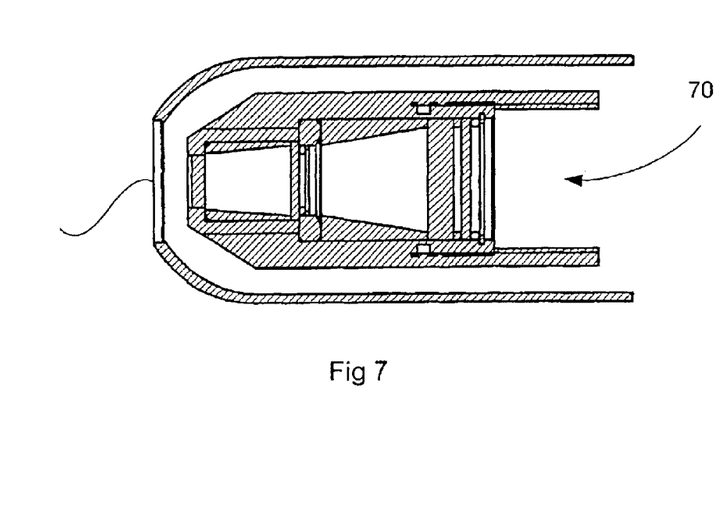
FIG. 7 is an enlarged sectional elevation of the distal end of the a monitoring sensor shown in FIG. 6.
Figure 8:
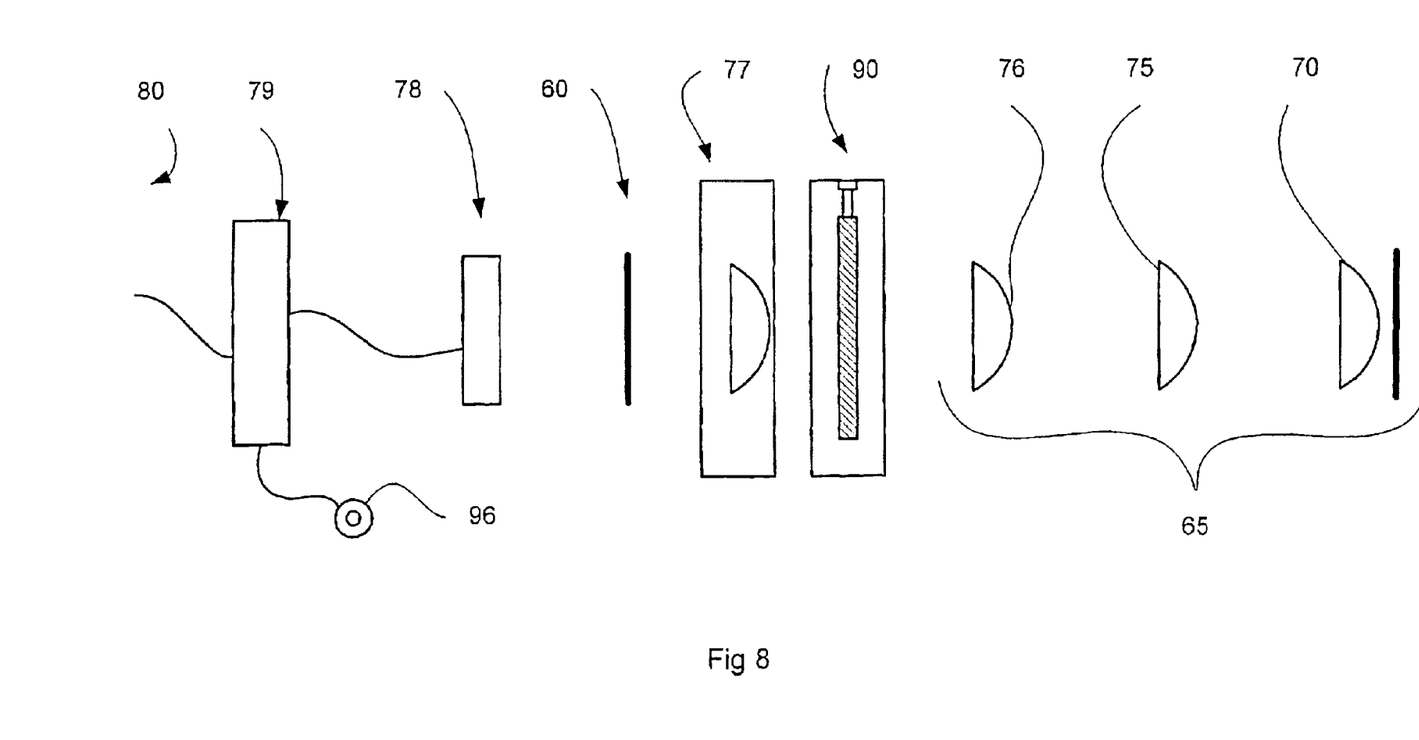
FIG. 8 is a schematic diagram of the optical elements in the sensor shown in FIG. 3.

The imaging optics consist of the double-layered steel lens tube 55, shown in FIGS. 5–7, containing a train of ZnSe or, amorphous silicon lenses 65. The front lens 70 serves as the objective, and has a field of view of at least 200. Three other lenses 75, 76 and 77 serve as transfer optics, transporting the image formed by the objective onto the focal plane array 78 of the camera 50. The electrical signals from the imaging array 78 are processed in the electronic circuitry 79 and transmitted to a remote processing system, in the case of the monitoring system shown in FIG. 2, or displayed on a display such as an LCD display screen 80 in the case of the hand-held unit shown in FIG. 3. The total length of the lens tube is about 36 inches, permitting the focal plane to be located remotely from the boiler port. The lens tube 55 is cooled and purged by a constant stream of air supplied at about 30 psi through a gas coupling 81 into the space between the inner and outer tubes of the double-layered lens tube 55, through which the air flows and exits out through an axial opening 85 at the distal end of the lens tube 65.

Several camera models could be used: a ferroelectric array camera, a PtSi camera, and a Si microbolometer array camera. Also, an InSb array camera operating in the 3.9 micron wavelength region, has produced adequate images but was determined to be impractical because of its cost and the limited lifetime of the necessary low temperature cooling systems required for operation of the camera. The ferroelectric array camera is attractive because it does not require cryogenic cooling, does not require frequent calibration and is relatively inexpensive. However, it does use a semi-transparent "chopper" wheel to limit the intensity of the light to the array. The chopper wheel introduces its own set of problems such as the superimposition of artifacts such as curved lines across the image. These problems can be addressed by changing required solutions to achieve satisfactory images. The PtSi array camera requires cryogenic cooling and is quite expensive, making it a less preferred version of the usable cameras. The microbolometer array camera does not require cryogenic cooling and does not use a chopper. It also has significantly greater dynamic range than the ferroelectric array camera. However, it may require frequent (once-a-day) re-calibration to produce acceptable images, and is significantly more expensive than the ferroelectric array camera.

The preferred camera is a ferroelectric array camera modified to view infrared radiation in a wavelength band of about 3.5–4.0 microns, preferably about 3.9 microns; or infrared radiation in a wavelength band of about 8.5–9.0 microns, preferably about 8.7 microns. This camera produces clear images in the system outlined above and is inexpensive enough to be affordable for pulp mills to purchase and use. We anticipate that other imaging arrays usable in our camera will be developed that will be usable in the system shown in FIG. 1

Figure 3:
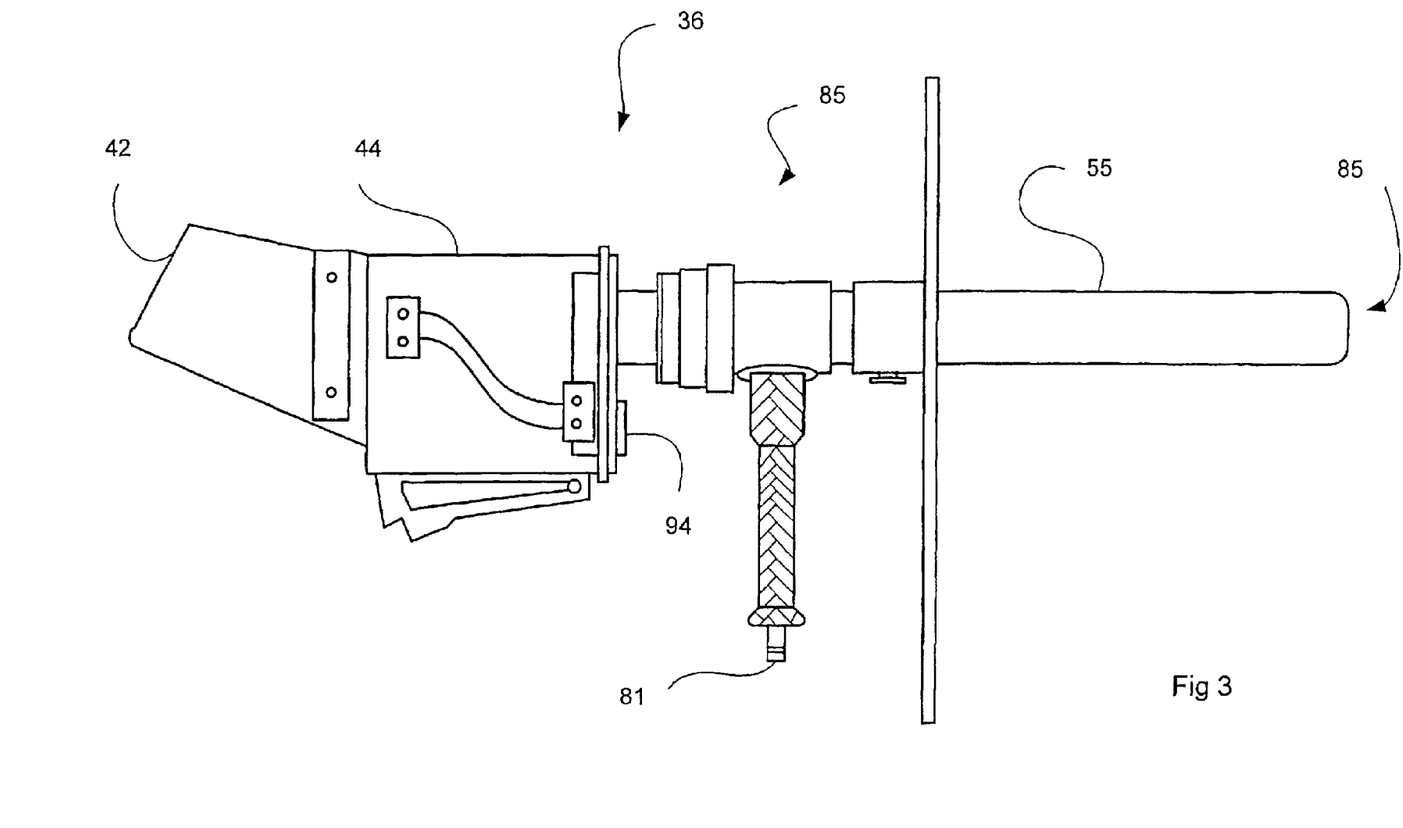
FIG. 3 is an elevation of a hand-held sensor in accordance with this invention.
Figure 4:
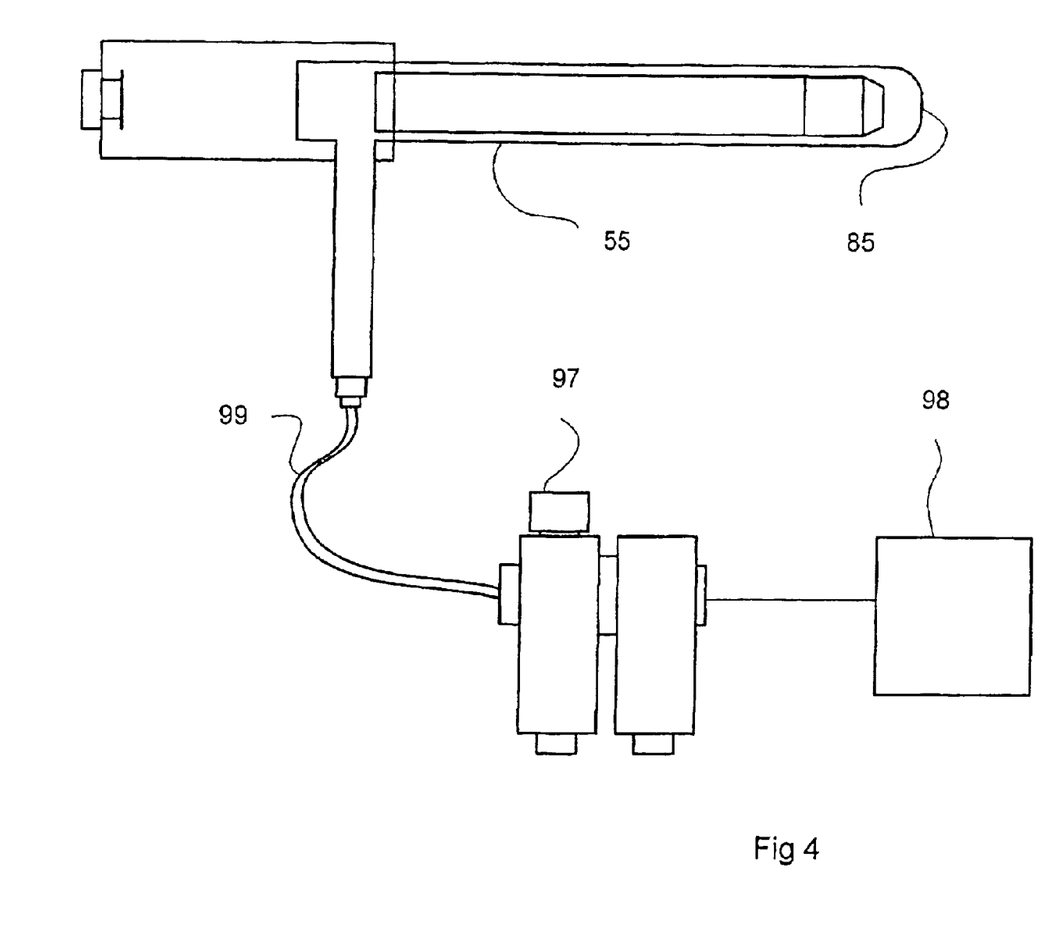
FIG. 4 is an elevation of the hand-held sensor of FIG. 3 showing the air flow system for the lens tube.

The sensor shown in FIG. 3 includes the camera body 44 connected to the lens tube 65 by way of an intermediate structure 85. The intermediate structure 85 includes an adjustable iris 90 and the lens 60, which is axially movable to give the lens train the ability of focus in a low-light, wide aperture condition. The hand-held unit 37 has a power switch 94 and an electrical connector 96, which provides the ability to connect electronically into the distributed control system 45. The lens tube 55 is connected to a source 98 of air pressure through a pressure regulator 97 and a flexible air hose 99.

Figure 9:
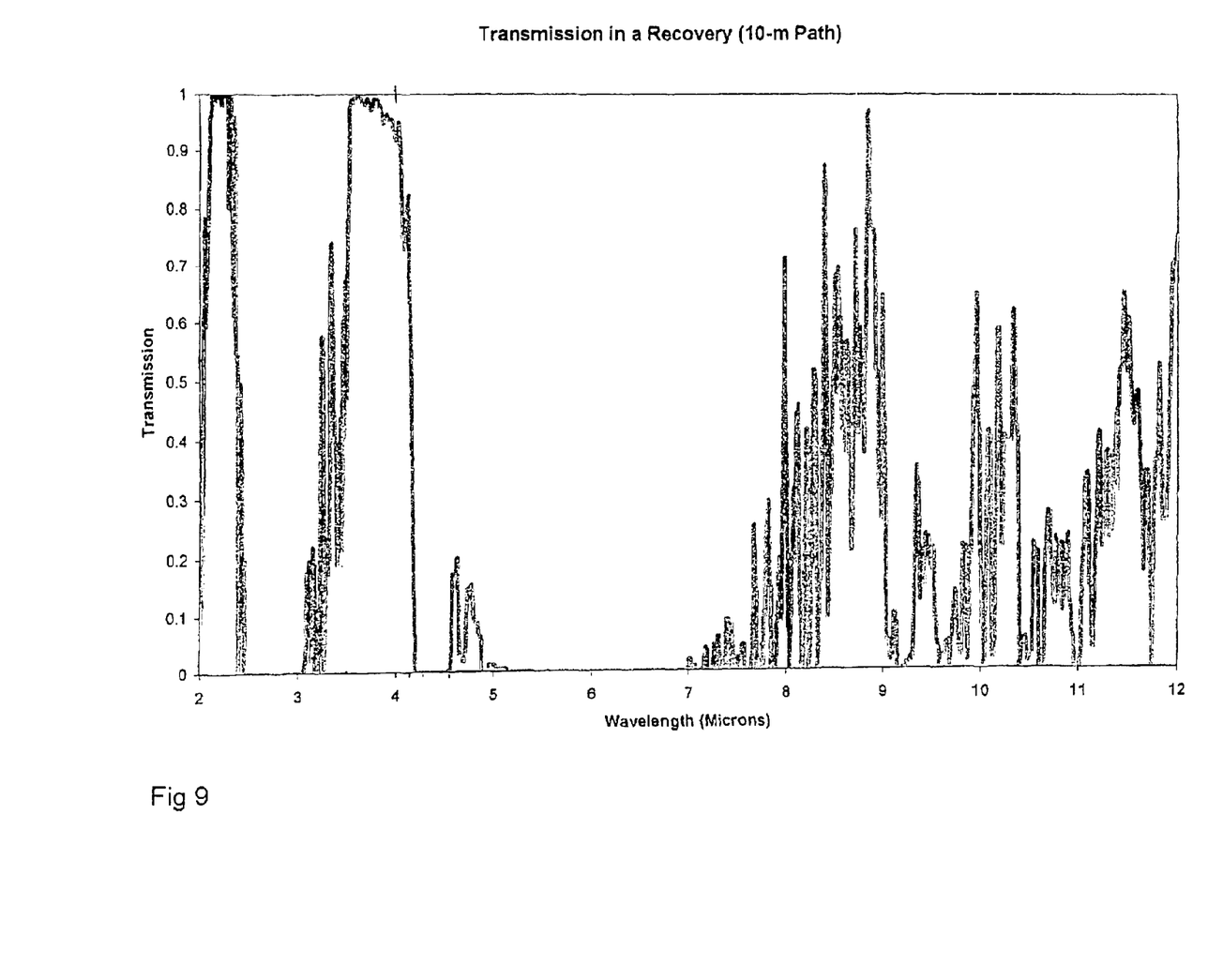
FIG. 9 is a graph showing the light transmission over a range of wavelengths in a recovery boiler.

The graph on FIG. 9 illustrates the benefits of operating in the regions of about 4 and 8.7 microns. As illustrated, there are several "windows" available to viewing the interior of a chemical recovery boiler by virtue of the light absorption characteristics of the gas and vapors in the gas stream of a chemical recovery boiler for a pulp mill. The visibility of the boiler interior at these wavelengths is also influenced by the scattering effect of the particles in the boiler gas. The effectiveness of this particle scattering is greatly decreased at longer wavelengths, and for wavelengths in excess of 3 microns does not significantly degrade images of recovery boiler interiors in the upper furnace and convection-pass sections. By operating an a region of low absorption and low scatter of the gas molecules and particles, respectively, in the boiler gas stream, the resolution of the images that are possible by infrared imaging in the chemical recovery boiler is maximized.

Figure 10:
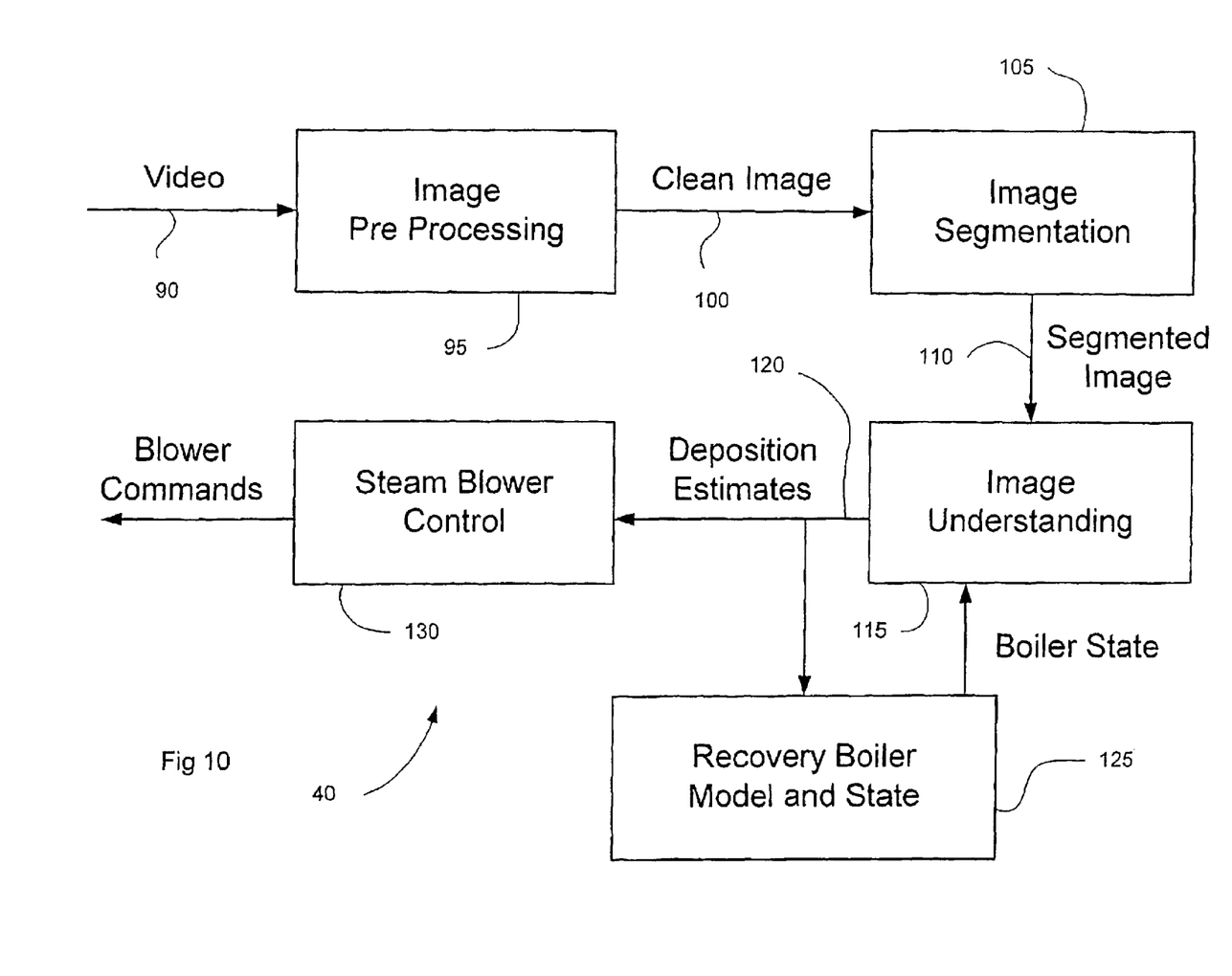
FIG. 10 is a schematic flow diagram of the process of receiving data from the monitoring sensors in FIGS. 1 and 3 to data input to the distributed control system in FIG. 1 for control of deposition control systems in the boiler.

Turning now to FIG. 10, an image processing system 40 and a link to one version of the distributed control system is shown having a video input 90 from the camera 50 to an image pre-processing circuit 95 in which the 2-D image is captured and noise filtering is performed in a low pass filter. Array compensation is accomplished to correct for pixel variation and dead cells, etc., and geometric distortion is corrected by image system compensation. A cleaned image 100 is sent from the image pre-processing circuit to an image segmentation module 105 where the image of the recovery boiler interior is separated into background, pendant tubes, and deposition. Thresholding/clustering on gray scale/texture is accomplished and morphological transforms to smooth regions are made. Regions are identified by connected components. The segmented image 110 is sent from the image segmentation module 105 to an image-understanding unit 115 where derived regions are matched to a 3-D model of the recovery boiler and a 3-D structure 120 of the deposition is inferred. Those deposition estimates can be provided to the distributed control system to update the computer model and state 125 of the recovery boiler which is fed back in a closed loop to continually update the image understanding unit 115. The deposition estimates 120 are fed to the "soot-blower" control 130 for optimized control of the steam cleaning system for the pendant tubes 49 in the boiler.

A control scheme is envisioned that utilizes the information from the deposition detection system to control or minimize further deposition, or optimize deposit removal processes. From the processed images, the system identifies the location of deposits and activates the steam cleaners, or "soot-blowers", that are most appropriate to clean the affected location and prevent pluggage. Currently, the "soot-blowers" are operated "blind" on a timed cycle. Operating only the soot-blowers only where and when there are deposits needing removal will minimize the steam usage as well as tube wear caused by unnecessary over-cleaning. Moreover, it is now possible for the first time to accurately relate the deposition rate to the liquor burning parameters, so the boiler operation can be optimized to minimize deposits on the pendant tubes.

Obviously, numerous modifications and variations of the preferred embodiment described above are possible and will become apparent to those skilled in the art in light of this specification. For example, many functions and advantages are described for the preferred embodiment, but in some uses of the invention, not all of these functions and advantages would be needed. Therefore, we contemplate the use of the invention using fewer than the complete set of noted functions and advantages. Moreover, several species and embodiments of the invention are disclosed herein, but not all are specifically claimed, although all are covered by generic claims. Nevertheless, it is our intention that each and every one of these species and embodiments, and the equivalents thereof, be encompassed and protected within the scope of the following claims, and no dedication to the public is intended by virtue of the lack of claims specific to any individual species. Accordingly, we expressly intend that all these embodiments, species, modifications and variations, and the equivalents thereof, are to be considered within the spirit and scope of the invention as defined in the following claims, wherein we claim:

What is claimed is:

1. A sensor data processing system for processing video data input from a camera aimed into the interior of a boiler and operating in the infra-red band, comprising:
   an image pre-processing circuit in which a 2-D image formed by said video data input is captured, and including a low pass filter for performing noise filtering of said video input, and having an image system compensation system for array compensation to correct for pixel variation and dead cells, etc., and geometric distortion is corrected;
   an image segmentation module for receiving a cleaned image sent from said image pre-processing circuit for separating said image of said recovery boiler interior into background, pendant tubes, and deposition, and for accomplishing thresholding/clustering on gray scale/texture and making morphological transforms to smooth regions, and for identifying regions by connected components;
   an image understanding unit for receiving a segmented image sent from said image segmentation module and for matching derived regions to a 3-D model of said boiler, and for deriving a 3-D structure the deposition on pendant tubes in said boiler is inferred.

2. A method for detection of deposition on pendant tubes in recovery and power boilers, comprising:
   collecting data from an infra-red video sensing system, operating in infrared wavelength regions of about 4 microns or about 8.7 microns, for detection of deposition on pendant tubes in recovery and power boilers and processing said sensor data in a sensor data processing system to identify specific quantities and regions of deposition, and delivering measures of said specific quantities and locations of said regions of deposition to a distributed control system by which said boilers are operated to clean said tubes more efficiently.

3. A method as defined in claim 2, further comprising:
   capturing a 2-D image formed by said video data in an image pre-processing circuit, and performing noise filtering of said video input in a low pass filter, and performing array compensation in an image system compensation system to correct for pixel variation and dead cells, etc., and correcting geometric distortion.

4. A method as defined in claim 3, further comprising:
   sending a cleaned image from said image pre-processing circuit to an image segmentation module and separating said image of said recovery boiler interior into background, pendant tubes, and deposition, and thresholding/clustering on gray scale/texture and making morphological transforms to smooth regions, and identifying regions by connected components.

5. A method as defined in claim 4, further comprising:
   sending a segmented image from said image segmentation module to an image understanding unit for matching derived regions to a 3-D model of said boiler, and deriving a 3-D structure of the deposition on pendant tubes in said boiler.

6. A method as defined in claim 5, further comprising:
   sending deposition data from said image understanding unit to a distributed control system to update a computer model and state of said boiler; and
   feeding said deposition data to "sootblower" control units in said boiler for optimized control of steam cleaning systems for pendant tubes in said boiler.

* * * * *